United States Patent [19]

Fenton

[11] Patent Number: 4,513,144

[45] Date of Patent: Apr. 23, 1985

[54] ACETAL PURIFICATION WITH SUPEROXIDES

[75] Inventor: Jeff T. Fenton, Ponca City, Okla.

[73] Assignee: Conoco Inc., Ponca City, Okla.

[21] Appl. No.: 438,672

[22] Filed: Nov. 3, 1982

[51] Int. Cl.$^3$ ............................................. C07D 323/06
[52] U.S. Cl. ..................................... 549/368; 549/347; 549/369; 549/430; 568/596; 568/598; 568/600; 568/603
[58] Field of Search ................ 549/368; 568/596, 598, 568/600, 603

[56] References Cited

U.S. PATENT DOCUMENTS

| | | | |
|---|---|---|---|
| 3,149,127 | 9/1964 | Platz | 549/368 |
| 3,470,208 | 9/1969 | Lasco et al. | 549/368 |
| 3,519,650 | 7/1970 | Fleck et al. | 549/368 |
| 3,580,928 | 5/1971 | McAndrew et al. | 549/368 |
| 3,607,882 | 9/1971 | Wenger | 549/368 |
| 4,026,873 | 5/1977 | Iguchi | 549/368 |
| 4,183,862 | 1/1980 | Steiner | 549/334 |
| 4,332,644 | 6/1982 | Hamanaka et al. | 549/368 |
| 4,423,238 | 12/1983 | Fenton | 549/368 |

FOREIGN PATENT DOCUMENTS

| | | | |
|---|---|---|---|
| 2806853 | 8/1978 | Fed. Rep. of Germany | 549/368 |
| 0006272 | 4/1966 | Japan | 549/368 |
| 0025502 | 11/1968 | Japan | 549/368 |

*Primary Examiner*—Ethel G. Love
*Attorney, Agent, or Firm*—Cortlan R. Schupbach

[57] ABSTRACT

Trioxane and other acetals are purified by contacting with an alkali metal superoxide, then isolated in a purified form. Optionally, a phase transfer catalyst can be utilized in the purification. Recovered acetals are sufficiently pure for polymerization to high molecular weight.

10 Claims, No Drawings

ACETAL PURIFICATION WITH SUPEROXIDES

This invention relates to a process for the purification of acetals. More specifically, this invention relates to a process for removing impurities from acetals by reacting the impurities with an alkali metal superoxide. Such impurities normally comprise water, formic acid, methyl formate, methanol and methylal. Optionally, phase transfer catalysts can be used to assist the superoxide.

Trioxane, which is the cyclic trimer of formaldehyde, is normally manufactured by heating aqueous formaldehyde solutions in the presence of a strong mineral acid such as sulfuric or hydrochloric acid. Unfortunately, the trioxane recovered from such a process contains impurities. These impurities include water, formic acid, methanol, methylal, methyl formate and the like. When trioxane containing these impurities is polymerized, some of the impurities act as chain transfer agents, thereby causing the resulting polymer product to have a lower molecular weight than otherwise possible when these impurities are absent. The molecular weight of the oxymethylene polymer obtained decreases as the amount of these impurities contained in the monomer feed increases. Impurities in trioxane can reach concentrations such that polymerization is severely retarded, or even totally prevented.

The major use for these acetals is in polymerization reactions. The presence of a small amount, such as 100 parts per million, of these impurities in the monomer feed causes sufficient chain transfer reactions to occur that the resulting molecular weight is not sufficiently high to provide a useful polymer.

Initially, attempts were made to purify acetals by distillation and recrystallization. However, such purification schemes do not sufficiently reduce the amount of impurities contained in the acetals to provide improved polymerization reactions unless such polymerizations and recrystallizations are carried out under stringent conditions and repeated several times, all of which make such a process economically prohibitive on a commercial basis.

Many attempts have been made in the art to improve the process of purifying acetals. U.S. Pat. No. 4,026,873 teaches the polyoxymethylene crystals prepared from trioxane wherein prior to polymerization the trioxane is purified by refluxing in the presence of sodium wire. U.S. Pat. No. 3,580,928 teaches a process for purifying acetals wherein the acetal is purified by contacting with liquid sodium, a precipitate is allowed to form and then removed from the solution. U.S. Pat. No. 3,607,882 deals with a method of removing impurities of trioxane and other acetals by forming an alkali metal ketyl which remains as a bottom after separation via distillation, and thus provides a purified acetal. However, this method is unsuitable since large quantities of ketones are required and large amounts of residue remain unless great care is taken. In addition, it has been found that attempts to use this procedure results in unpredictable quality during the removal of the impurities.

U.S. Pat. No. 3,519,650 and European Patent Application No. 36522 relates to the purification of trioxane by treating the trioxane with an aqueous alkaline reagent such as sodium hydroxide and potassium hydroxide. U.S. Pat. No. 3,149,127 treats impure trioxane with potassium oxide. U.S. Pat. No. 3,560,526 treats substituted trioxane with sodium oxide. U.S. Pat. No. 3,281,336 purifys trioxane by extractively distilling the same with ethylene or propylene glycol. However, all of these methods are unsuitable from a quality or cost effectiveness standpoint.

It would therefore be of great benefit to provide an improved method wherein a rapid, economical removal of impurities from acetal such as trioxane can be carried out.

It is therefore an object of the present invention to provide an improved process for the removal of impurities from acetals such as trioxane. Other objects will be apparent to those skilled in this art as the description proceeds.

The present invention can be carried out quickly and easily, but must be carried out under substantially anhydrous conditions. It would, of course, be preferably to carry out the present invention under a dry inert atmosphere, but an inert atmosphere is not critical to the success of the present invention.

After the impurities have been reduced utilizing alkali metal superoxides, the alkali metal residues remain behind with the impurity residues after filtration or fractional distillation. The resultant recovered acetals are extremely pure and useful.

Normally, the process of the instant invention is carried out at a temperature sufficient to place the acetals to be purified in a molten state. Any temperature above this may be used as desired, but it is clearly more convenient to utilize the lowest temperature consistent with maintaining the acetals in a molten condition.

The process of the present invention can be carried out for a time ranging from about 15 minutes to about 24 hours, but normally times ranging from about 1 hour to about 5 hours will be used and times ranging from about 1 hour to 2 hours is preferred.

Normally, from about 0.5 to about 10 weight percent of alkali metal superoxide, based on the weight of acetal present, will be used, but from about 1 to about 5% is preferred.

Acetals which can be purified using the process of the present invention are those having the general structure

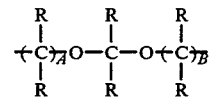

wherein A and B are numbers from about 1 to about 3, R is hydrogen or a hydrocarbon radial having from 1 to about 20 carbon atoms, cyclic, aliphatic or aromatic radicals having from 6 to about 20 carbon atoms, or mixtures of these. The present invention comprises contacting said trioxane or acetal or mixtures of these with an alakli metal superoxide, optionally in the presence of a phase transfer catalyst, refluxing for a time sufficient to react with impurities present, and removing the reduced alkali metal, and phase transfer catalyst is used.

I have now discovered according to the present invention that acetals containing impurities such as water, alcohols and aldehydes or mixtures of these are purified by placing said acetals into a molten state and contacting said molten acetals under anhydrous conditions with an alkali metal superoxide for a time to reduce the impurities present and then recovering the purified acetals.

In the prior art the use of alkali metals such as described in U.S. Pat. No. 4,026,873 satisfactorily removed impurities from the acetals. However, such a reaction requires vigorous and lengthy refluxing. In contrast, the superoxides of the present invention provide an efficient and reliable method for purifying acetals.

The alkali metal superoxides of the present invention have the general formula $MO_2$ wherein M represents any alkali metal. The amount of superoxide used, the length of contact time and the temperature will, of course, depend upon the impurity level in the trioxane. After the impurities have been reduced by the alkali metal superoxide, trioxane can be recovered by any conventional technique. Examples of conventional techniques known to those skilled in the art are filtration, distillation, flash distillation and the like, with flash distillation being the preferred technique. Purified acetals are then suitable for any desired purpose, but are especially useful for polymerization to high molecular weight.

I have further discovered that in addition to the alkali metal superoxide, an effective amount of a phase transfer catalyst can likewise be added to the reaction mixture in order to enhance the purification procedure. I have disclosed the use of phase transfer catalysts with alkali metals to purify acetals in my co-pending patent application Ser. No. 378,660, filed May 17, 1982. The use of a phase transfer catalyst reduces the reaction time since the alkali metal superoxides are in a completely different state than the impurities. This difficulty is resolved by the process of the present invention which optionally utilizes, in addition to the alkali metal superoxides, a phase transfer catalyst in order to make the reaction more efficient, achieve completion more quickly and provide low levels of residue after well-known separation techniques.

Representative examples of acetals which may be purified using the method of the present invention are trioxane, tetraoxane, 3-dioxane, 4-methyl-1,3-dioxolane, 1,3-dioxolane, 1,3,5-trioxacyclooctane, 1,4-butane-diol-formal, 1,4-butenediolformal, methoxymethylal, methylal and dimethoxymethylal. The present invention is especially effective with trioxane, which is polymerizable in and of itself or can be copolymerized with other monomeric compounds to form polyoxymethylene polymers and copolymers.

The acetals treated using the method of the present invention can contain high amounts of impurities, i.e. 5 weight percent or more based upon the weight of the acetal. Normally, as produced, such acetals will contain from about 0.05 to about 5.0 weight percent of such impurities. Water and methanol are usually the predominant impurities.

The alkali metal superoxides useful in the present invention have the formula $MO_2$ where M is sodium, potassium and lithium, and of these sodium and potassium are more preferred with potassium being the most preferred metal. Mixtures of metal superoxides may also be used, for example sodium potassium superoxides are useful in the present invention.

Phase transfer catalysts are optionally used as provided in the present invention. The phase transfer catalyst will normally be present in concentrations of from about 0.01 to about 10 weight percent based on the weight of acetal being purified. Phase transfer catalysts useful in the process of the present invention include crown ethers, cryptates and analogues of these, as well as quaternary salts and ethers.

The phase transfer catalysts useful in the process of the present invention are thus those which are effective in promoting the reaction between impurities and the alkali metal superoxides. Phase transfer catalysts are effective when, in a system of two phases, the phase transfer agent in catalytic quantity brings one reactant from its normal phase into the phase of a second reactant such that reaction between the two can occur with reasonable speed. In principle transfer of species may be any chemical agent, but normally organic phases will be used.

Both macrocyclic (crown ether) materials and macrobicyclic (cryptate materials) are useful in the practice of the present invention. These materials are normally extremely complex and have no encompassing general formulas. However, representative but non-exhaustive examples of crown ethers useful in the practice of the present invention include 15-crown-5-ether, 18-crown-6-ether, dibenzo-18-crown-6 ether, dicyclohexyl-18-crown-6-ether, benzo-15-crown-5 ether, alkyl-18-crown-6-ether, alkyl-2,2,2-cryptate ether, benzo-2,2,2-cryptate, 2,2,2-cryptate, 2,2,1-cryptate, 2,1 1-cryptate, dibenzo-24-crown-6, and 12-crown-4.

Crown ethers are chosen depending on the alkali metal used. That is, 12-crown-4 is best for lithium, 15-crown-5 for sodium, and 18-crown-6 for potassium. Mixtures of metals would require, optimally, a mixture of crown ethers. Cryptates and polyethers are less specific since they contain flexible linkages allowing these materials to "wrap" around the metal ion.

In addition, analogues of crown ethers and cryptates containing nitrogen or sulfur atoms are also useful in the practice of the present invention as they have donor properties to the crown ethers containing only carbon oxygen in the linkages. Representative examples of structures of such analogues are described.

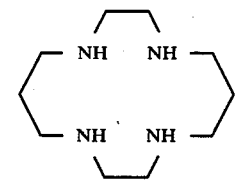

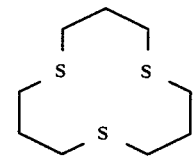

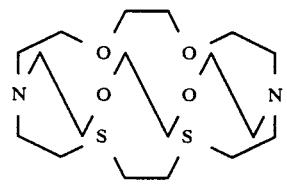

-continued

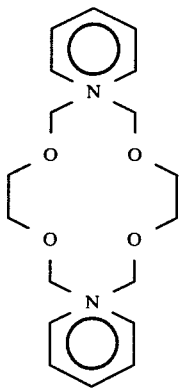

Polyethers of the general formula

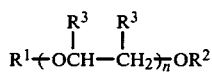

where $R^1$, $R^2$, and $R^3$ are, independently, hydrogen atoms or alkyl radicals containing from 1 to 20 carbon atoms and n is greater than 1 are useful as phase transfer catalysts in the present invention.

Representative but non-exhaustive examples of polyethers useful in the present invention are polyethylene glycols of varying molecular weight of the formula $HO-(CH_2CH_2O)_nH$ where n is from 1 to 14, glyme, diglyme, triglyme, tetraglyme, propylene glycol methyl ether, diethylene glycol methyl ether, diethylene glycol n-butylether. Mixtures of these catalysts can be used.

Also useful are quaternary salts of the general formula $X(MR^1R^2R^3R^4)$ where M is nitrogen, phosphorus, arsenic antimony or bismith, X is an anion which will dissociate from the cation in an aqueous environment, and $R^1$, $R^2$, $R^3$ and $R^4$ are monovalent hydrocarbon radicals consisting of alkyl, alkenyl, aryl, alkaryl, aralkyl and cycloalkyl radicals. X is preferably halide and hydroxyl ions. Generally each R can contain from about 1 to about 25 or more carbon atoms each. The total carbon atom content of all these groups has no theoretical upper limit, although about 70 carbon atoms constitutes a product having a practical upper limit imposed by economic factors. It is also highly preferred that each of the hydrocarbon substituents $R^1$, $R^2$, $R^3$, and $R^4$, contain more than a single carbon atom.

Representative but non-exhaustive examples of suitable quaternary salts are hexadecyltrihexylammonium bromide; trioctylethylammonium bromide; tridecylmethylammonium chloride; didodecyldimethylammonium chloride; tetraheptylammonium iodide; dioctadecyldimethyl ammonium chloride; tridecylbenzylammonium chloride; ditricosylmethylammonium chloride; tributyldecylphosphonium iodide; triphenyldecylphosphonium iodide, tributylhexadecylphosphonium iodide; tricaprylyldodecylammonium p-toluene sulfonate; tribenzyldecylarsonium chloride; tetranonylammonium hydroxide; tritridecylphenylstibonium chloride; triahentriacontylmethylbismuth chloride; N,N,N'N'-tetramethyl-N,N'-ditetradecyl-p-xylene-α,α'-diammonia dichloride; 1-methyl-1-(N-octadecanoyl-2-minoethyl)2-heptadecyl-4,5-dihydro-1,3-diazole methylsulfate; N,N,N',N'-tetramethyl-N,N'-dioctadecyl-x-dodecyl-y-xylene α,α'-diammonium dichloride; N,N-dioctadecyl-N-methyl-N-(sodiocarboxylmethyl)-ammonium chloride, N,N,N',N'-tetramethyl-N,N'-dioctadecyl-p-xylene-α,α'-diammonium dichloride; N,N,N',N'-tetramethyl-N,N'-dioctadecyl-1,2-ethyl-diammonium dibromide; N,N'-dimethyl-N,N,N',N'-tetraheptadecyl-2-butene-1,4-diammonium chloride.

Normally, the impurities are converted to alkali salts which are normally solids and can be separated from the acetal by sedimentation, filtration, distillation and the like. However, depending upon the phase transfer catalyst used, normally distillation or fractionation is the preferred method since these methods remove the catalysts from the system with reduced alkali metal. However, the process of the present invention requires only one distillation to be totally effective in removing sufficient impurities to allow polymerization to proceed to high levels.

The invention is more concretely described with reference to the examples below wherein all parts and percentages are by weight unless otherwise specified. The examples are provided to illustrate the present invention and not to limit it.

EXAMPLE 1

Commercial trioxane, 226 g, was placed in a 3-neck round bottom flask fitted with a Friedrichs condensor, flushed with argon, melted, and refluxed with stirring for 4.5 hours. An air-cooled condensor was attached and 204.2 g were removed by distillation into a dry, argon flushed, one liter jacketed resin kettle. The distilled trioxane was melted by 70° C. circulating water to a clear melt, and thereafter 6.8 ml of ethylene oxide (2.97 wt.% based on trioxane) were added to the kettle. To the stirred melt was added 3.6 ml of a 0.03113M solution of $BF_3.OEt_2$ in anhydrous methylene chloride. After 1 hour 45 minutes, no polymerization reaction had occurred.

EXAMPLE 2

Commercial trioxane (225 g) in an argon flushed flask was contacted with 10 g of potassium superoxide ($KO_2$). This mixture was refluxed as in Example 1 for 4 hours, after which 168.9 g of trioxane were distilled into a dry, argon flushed resin kettle. The trioxane was melted at 70° C. and mixed with 5.7 ml (3.01 wt.%) ethylene oxide. Reaction was initiated with 3.0 ml of the 0.03313M $BF_3.OEt_2$ solution. Polymerization to a solid mass occurred after a 13 minute 33 second induction period. The inherent viscosity of the resultant copolymer was 0.82 deciliters per gram (dl/g).

EXAMPLE 3

Commercial trioxane (22 g) in an argon flushed flask was contacted with 10 g of $KO_2$ and about 1–1.5 g of 18-crown-6. This mixture was refluxed for 4 hours, after which 185.3 g were distilled into a dry, argon flushed resin kettle. The trioxane was melted at 70° C. and 6.2 ml (2.98 wt%) ethylene oxide was added. Polymerization was initiated with 3.3 ml of the $BF_3.OEt_2$ solution and the reaction solidified after an 18 minute 3 second induction period. The inherent viscosity of the isolated copolymer was 0.56 dl/g.

EXAMPLE 4

Commercial trioxane is refluxed for from ca. 0.5–24 hours over pellets of potassium superoxide ($KO_2$), 5–10 g, under an inert atmosphere. The superoxide anion, $O_2-$, reduces undesired impurities to insoluble potassium salts and then is released as oxygen gas. The trioxane after reflux is then isolated by flash distillation and condensed. Upon melting, the trioxane shows no signs of polymer formation, an indication of excellent purity, and is polymerized to high molecular weight.

While certain embodiments and details have been shown for the purpose of illustrating this invention, it will be apparent to those skilled in this art that various changes and modifications may be made herein without departing from the spirit or scope of the invention.

I claim:

1. A method for purifying acetals comprising
   (1) placing said acetals into a molten state,
   (2) contacting molten acetals with alkali metal superoxides under substantially anhydrous conditions for a time sufficient to reduce impurities present, and
   (3) recovering the purified acetal.

2. A method as described in claim 1 wherein the acetals are contacted for a time ranging from about 15 minutes to about 24 hours in the presence of from about 0.5 to about 10 weight percent of alkali metal superoxide.

3. A method as described in claim 2 wherein the acetal is recovered by filtration or distillation.

4. A method as described in claim 3 wherein the acetal is trioxane and the alkali metal superoxide is potassium superoxide.

5. A method as described in claim 1 wherein step 2 is carried out in the presence of a phase transfer catalyst.

6. A method as described in claim 5 wherein the phase transfer catalyst is present in concentrations of from about 0.1 weight percent to about 10 weight percent based on the acetal present.

7. A method as described in claim 6 wherein the acetal is at least one material selected from the group consisting of trioxane, tetraoxane, 1,3-dioxane, 3-dioxane 4-methyl-1,3-dioxolane, 1,3-dioxolane, 1,3,6-trioxacyclooctane, 1,4-butane-diolformal, 1,4-butenediolformal, methoxymethylal, methylal and dimethoxymethylal.

8. A method as described in claim 7 wherein the phase transfer catalyst is at least one crown ether selected from the group consisting of 15-crown-5-ether, 18-crown-6-ether, dibenzo-18-crown-6 ether, dicyclohexyl-18-crown-6-ether, benzo-15-crown-5-ether, alkyl-18-crown-6-ether, alkyl-2,2,2-cryptate ether, benzo-2,2,2-cryptate, 2,2,2-cryptate, 2,2,1-cryptate, 2,1,1-cryptate, dibenzo-24-crown-6, and 12-crown-4.

9. A method as described in claim 7 wherein the phase transfer catalyst is at least one polyether selected from the group consisting of $HO-(CH_2CH_2O)_nH$ where n is from 1 to 14, glyme, triglyme, tetraglyme, diglyme, propylene glycol methyl ether, diethylene glycol, methyl ether and diethylene glycol n-butyl ether.

10. A method as described in claim 7 wherein the phase transfer catalyst is a quaternary salt selected from the group consisting of hexadecyltrihexylammonium bromide; trioctylethylammonium bromide; tridecylmethylammonium chloride; didodecyldimethylammonium chloride; tetraheptylammonium iodide; dioctadecyldimethyl ammonium chloride; tridecylbenzylammonium chloride; ditricosylmethylammonium chloride, tributyldecylphosphonium iodide; triphenyldecylphosphonium iodide, tributylhexadecylphosphonium iodide; tricaprylyldodecylammonium p-toluene sulfonate; tribenzyldecylarsonium chloride; tetranonylammonium hydroxide; tritridecylphenylstibonium chloride; triahentriacontylmethylbismuth chloride; N,N,N'N'-tetramethyl-N,N'-ditetradecyl-p-xylene-α,α'-diammonia dichloride; 1-methyl-1-(N-octadecanoyl-2-minoethyl)2-heptadecyl-4,5-dihydro-1,3-diazole methylsulfate; N,N,N',N'-tetramethyl-N,N'-dioctadecyl-x-dodecyl-y-xylene α,α'-diammonium dichloride; N,N-dioctadecyl-N-methyl-N-(sodiocarboxylmethyl)-ammonium chloride, N,N,N',N'-tetramethylN,N'-diotadecyl-p-xylene-α,α'-diammonium dichloride; N,N,N',N'-tetramethyl-N,N'-dioctadecyl-1,2-ethyl-diammonium dibromide; N,N'-dimethyl-N,N,N',N'-tetraheptadecyl-2-butene-1,4-diammonium chloride.

* * * * *